(12) United States Patent
Meier et al.

(10) Patent No.: US 6,437,009 B1
(45) Date of Patent: Aug. 20, 2002

(54) LOW FOAM N-ALKYLTARTARIMIDE AND N-ALKYLMALIMIDE WETTING AGENTS

(75) Inventors: Ingrid Kristine Meier, Asbury, NJ (US); Kevin Rodney Lassila, Macungie; Caroline Sassano Slone, Quakertown, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/820,446

(22) Filed: Mar. 29, 2001

(51) Int. Cl.$^7$ .................. B01D 12/00; C07D 207/36; C07D 207/40; A61K 7/075
(52) U.S. Cl. .................. 516/203; 548/544; 548/545; 548/547; 424/70.19
(58) Field of Search .................. 424/70.19; 548/545, 548/544, 547; 516/203

(56) References Cited

U.S. PATENT DOCUMENTS

| | | | |
|---|---|---|---|
| 4,237,022 A | 12/1980 | Barrer | 252/51.5 A |
| 4,996,330 A | 2/1991 | Scherowsky et al. | 548/544 |
| 5,554,768 A * | 9/1996 | Donges et al. | 548/545 |
| 6,281,170 B1 * | 8/2001 | Marsella et al. | 504/362 |

FOREIGN PATENT DOCUMENTS

| | | |
|---|---|---|
| JP | 04029970 | 1/1992 |
| JP | 04029971 | 1/1992 |
| JP | 10121090 | 5/1998 |
| JP | 11050098 | 2/1999 |

OTHER PUBLICATIONS

English language translation of Ueda (JP 10–121090, published May 1998).*
Padget, J. C., "Additives for Water–Based Coatings—A Polymer Chemist's View", Additives for Water–Based Coatings, D. R. Karsa, ed., Cambridge UK: Royal Society of Chemistry, 1990, pp.1–29.
Dispersions: Characterization, Testing and Measurement, Marcel Dekker, Inc. 1990.
Kubler, R., "Printing Inks" Ulmann's Encyclopedia of Industrial Chemistry Technology, 4$^{th}$ Edition, Vol. A22, 1993, pp. 143–156.
Bassemir, R. W., et al., "Inks" Kirk–Othmer Encyclopedia of Chemical Technology, 4$^{th}$ Edition, Vol. 14, pp. 482–503.
Sheats, J., R., Smith B. W. "Microlithography, Science and Technology" Marcel Dekker, Inc. 1998, pp. 551–553.

* cited by examiner

Primary Examiner—Michael G. Hartley
Assistant Examiner—Michael A. Willis
(74) Attorney, Agent, or Firm—Michael Leach

(57) ABSTRACT

This invention provides water-based compositions, particularly coating, ink, fountain solution, adhesive, agricultural and electronics cleaning compositions, manifesting reduced equilibrium surface tension by the incorporation of a surface tension reducing amount of an N-alkylimide of tartaric acid and/or an N-alkylimide of malic acid of the following structures, respectively:

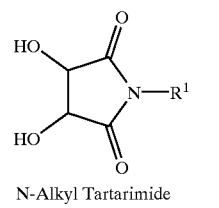 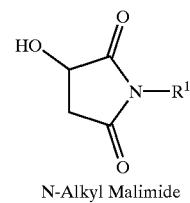

N-Alkyl Tartarimide    N-Alkyl Malimide where $R^1$ is a C5 to C10 alkyl group.

10 Claims, No Drawings

LOW FOAM N-ALKYLTARTARIMIDE AND N-ALKYLMALIMIDE WETTING AGENTS

FIELD OF THE INVENTION

The invention relates to the use of N-alkyltartarimides and N-alkylmalimides to reduce the surface tension in water-based systems.

BACKGROUND OF THE INVENTION

The ability to reduce the surface tension of water is of great importance in waterborne coatings, inks, adhesives, fountain solutions and agricultural formulations because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important measure of the ability of a surfactant to reduce surface tension in aqueous systems when the system is at rest.

Traditional nonionic surfactants, such as alkylphenol or alcohol ethoxylates and ethylene oxide (EO)/propylene oxide (PO) copolymers, and anionic surfactants, such as sodium dialkyl sulfosuccinates, have good equilibrium surface tension performance. However, many of these surfactants are foamy and this can lead to problems in applications such as coatings, inks, adhesives, fountain solutions, agricultural formulations, electronic chemicals and cleaning formulations, and other applications where foam can lead to surface defects, poor adhesion, and processing difficulties. Additionally, anionic surfactants can impart water sensitivity to the finished coating.

In addition to the development of high-performance surfactants, there is considerable interest in the industry in surfactants with improved environmental characteristics. Environmental concerns have led to an increased use of environmentally compatible surfactants as alternatives have become available. In addition, the use of less favorable products, such as alkylphenol ethoxylate (APE) surfactants, has declined. This is, in part, due to the poor environmental characteristics of APE surfactants, such as incomplete biodegradation and a suspicion that they may function as endocrine mimics. The demand for high-performance, eco-friendly surfactants has stimulated efforts in new surfactant development. From this work a new family of surfactants, referred to as alkyl polyglycoside (APG) surfactants, has emerged as a readily biodegradable, environmentally-friendly alternative to conventional surfactants. These materials can be foamy and thus are not suitable for many coating, ink, adhesive, fountain solution, agricultural, and electronic chemical and cleaning applications where the generation of foam is undesirable.

Thus, not only is it desirable to obtain surfactants which exhibit excellent surface tension reducing capabilities and low foam, but it is also highly desirable that such new surfactants are environmentally-friendly. Moreover, since there is substantial interest in the development of environmentally-friendly surfactants, an essential attribute would be that these new surfactants not only possess the aforementioned desired performance properties but also are derived from naturally occurring compounds or their synthetic equivalents.

The importance of reducing surface tension in applications such as coatings, inks, adhesives, agricultural formulations, and electronic chemical and cleaning is well-appreciated in the art. The ability to lower the surface tension of aqueous media without producing foam is critical when one wants to wet low energy or contaminated substrates. In J. C. Padget's article entitled "Additives for Water-based Coatings—A Polymer Chemist's View" in *Additives for Water-based Coatings*, D. R. Karsa, ed., Cambridge, UK: Royal Society of Chemistry, 1990, pp. 1–29, the importance of surfactants in lowering the surface tension of aqueous systems in order to achieve wetting on low energy materials such as plastics and oily steel is highlighted.

In the graphic arts, it is well-known that surfactants lower the surface tension of aqueous media and thus aid in printing on lower energy substrates such as plastics, coated papers, coated cardboards, and foils and in wetting pigments to produce dispersions. In *Dispersions: Characterization, Testing, and Measurement*, Marcel Dekker, Inc., 1990, there is an entire chapter devoted to the topic of wettability and the necessity of lowering surface tension in order to achieve displacement of air from around small pigment particles and allow wetting and spreading on the pigment surface. Surfactants are known to act as wetting agents to moisten hydrophobic areas of the printing plate in offset printing (R. Kubler, "Printing Inks," in *Ullmann's Encyclopedia of Industrial Chemistry*, Vol. A22, 1993, pp. 143–156), and certain surfactants have been beneficial in reducing foam generation in the ink fountain in flexographic and rotogravure printing inks (R. W. Bassemir, et al., "Inks," in *Kirk-Othmer Encyclopedia of Chemical Technology*, $4^{th}$ Edition, Vol. 14, pp. 482–503).

In addition, the demands of the semiconductor fabrication industry have led to the requirement for high performance surfactants and wetting agents for photoresist developer formulations. As line features shrink to smaller sizes and photoresist substrate materials become more aliphatic in nature (i. e., lower surface energy), aqueous developer solutions increasingly are being formulated with surface tension reducing agents. An additional requirement for these developers, accentuated by the move toward larger wafer sizes, is that they exhibit low foam. This is particularly important when the so-called spray puddle techniques are used in applying the developer solution, wherein the developer is sprayed over increasingly larger areas. Even in cases where puddle or immersion techniques are used, microbubble entrainment during spreading of the solution over the photoresist surface can lead to defects. Other applications in the electronics industry using aqueous processing media would also benefit from good wetting and low foam.

Tetramethylammonium hydroxide (TMAH) is the chemical of choice in aqueous alkaline solutions for developing photoresists according to *Microlithography, Science and Technology*, J. R. Sheats and B. W. Smith, editors, Marcel Dekker, Inc.; 1998, pp. 551–553. Surfactants are added to the aqueous TMAH solutions to reduce development time and scumming and to improve surface wetting.

Imides of tartaric acid (2,3-dihydroxy butanedioic acid), also called tartarimides, are known. L-Tartaric acid occurs naturally in grapes and is produced from the residues deposited in fermentation vats during wine making. It is classified as GRAS (Generally Recognized As Safe) by the U.S. Food and Drug Administration and is commonly used by the food, pharmaceutical and viniculture industries. The racemic form, DL-tartaric acid, is also known. It is produced by maleic acid oxidation or L-tartaric acid racemization.

A few examples of imides of malic acid (2-hydroxybutanedioic acid), also called malimides, are known. L-Malic acid occurs naturally as the predominant acid in many fruits. It is classified as GRAS (Generally Recognized As Safe) by the U.S. Food and Drug Administration and is commonly used as a food acidulant. L-Malic acid is produced commercially from aqueous fumaric acid using immobilized *Brevibacterium flavum* cells in carrageenan. The racemic form, DL-malic acid, is also known. It is produced by hydration of maleic acid at elevated temperature and pressure.

In the literature, tartaric acid and malic acid imides are known. However, the ability of tartarimides and malimides to lower surface tension in aqueous media, has not been realized.

U.S. Pat. No. 4,237,022 discloses the compositions of tartarimides having up to 150 carbon atoms in the hydrocarbon-based chain. These tartarimides were found to be useful as additives in lubricants and fuels.

U.S. Pat. No. 4,996,330 discloses the use of certain tartarimides as intermediates in the synthesis of new chiral N-substituted tartarimides which are esterified on both of the hydroxyl groups (pyrrolidinediones).

JP 04029970 A and JP 04029971 A disclose methods for preparing tartarimides containing alkyl groups of up to 20 carbon atoms. The tartarimides described therein are reported to be useful as heat resistance improvers and modifiers for polymers in non-aqueous applications.

JP 10121090 A discloses a detergent composition that comprises at least two ingredients, the first of which may be a tartarimide or malimide containing a C8–C22 alkyl group. The second essential ingredient in the detergent composition is a surfactant that acts as a detergent. The composition has high detergency, foaming power, and foam quality that is useful as a body shampoo, shampoo, kitchen detergent and soap.

JP 11050098 A discloses a solid soap composition that contains at least three ingredients, the first of which may be a hydroxycarboxylic imide. The second and third essential ingredients in the solid soap composition are an acyl isethionic acid or its salt and a soap.

SUMMARY OF THE INVENTION

This invention provides water-based compositions containing an organic or inorganic compound, particularly aqueous organic coating, ink, adhesive, fountain solution, agricultural and electronics cleaning compositions, having reduced surface tension by incorporation of an effective amount of an N-alkylimide of tartaric acid, herein referred to as a tartarimide, and/or an N-alkylimide of malic acid, herein referred to as a malimide, of the following structures, respectively:

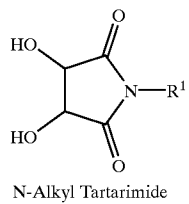 

N-Alkyl Tartarimide    N-Alkyl Malimide where $R^1$ is a C5 to C10 alkyl group. It is also desirable that an aqueous solution of the tartarimide or malimide demonstrates an equilibrium surface tension of less than 52 dynes/cm at a concentration of no more than 5 wt % in water at 25° C. using the Wilhelmy plate method. The Wilhelmy plate method of measuring surface tension is described in L. Wilhelmy's article in *Ann. Phys.* 1863, 119, 177, which is incorporated by reference.

By "water-based", "aqueous" or "aqueous medium", we mean, for purposes of this invention, a solvent or liquid dispersing medium which comprises at least 90 wt %, preferably at least 95 wt %, water. Obviously, an all water medium is also included.

Also provided is a method for lowering the equilibrium surface tension of such aqueous compositions by the incorporation of these tartarimide or malimide compounds.

Also provided is a method for applying a coating of a water-based inorganic or organic compound-containing composition to a surface to partially or fully coat the surface with the water-based composition, the composition containing an effective amount of a tartarimide or malimide compound of the above structure for reducing the equilibrium surface tension of the water-based composition.

There are significant advantages associated with the use of these tartarimides and malimides in water-based, organic-compound containing compositions, such as water-based coatings, inks, adhesives, fountain solutions, agricultural formulations, and electronic chemical and cleaning formulations, including photoresist developer compositions, and these advantages include:

water-borne coatings, inks, adhesives, fountain solutions, agricultural formulations, and electronic chemical formulations which may be applied to a variety of substrates with excellent wetting of substrate surfaces;

a reduction in coating or printing defects such as orange peel and flow/leveling deficiencies;

low surface tension aqueous electronics cleaning and processing solutions, including photoresist developer solutions, which provide good wetting and very low foam;

low-foam surfactants capable of reducing surface tension;

water-borne compositions using a surfactant derived from natural, renewable resources, thus making such formulations environmentally favorable.

Because of their surfactant properties and the ability to control foam, these materials are likely to find applicability in many applications in which the reduction in surface tension and low foam are important. Such applications in which low foam is important include various wet-processing textile operations, such as the dyeing of fibers, fiber scouring, and kier boiling, where low-foaming properties would be particularly advantageous; they may also have applicability in soaps, water-based perfumes, shampoos, detergents, cosmetics and food processing where their marked ability to lower surface tension, and at the same time produce little to no foam would be highly desirable.

DETAILED DESCRIPTION OF THE INVENTION

This invention relates to the use of N-alkylimide compounds of the structures:

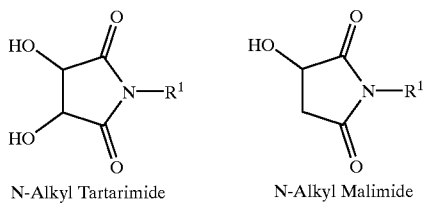

N-Alkyl Tartarimide        N-Alkyl Malimide where $R^1$ is a C5 to C10 alkyl group, preferably C7 to C10, and most preferably C8 to C10, for the reduction of equilibrium surface tension in water-based compositions containing an organic compound, particularly coating, ink, fountain solution, adhesive, agricultural, and photoresist developer compositions containing organic compounds such as polymeric resins, detergents, herbicides, fungicides, insecticides or plant growth modifying agents. It is also desirable that an aqueous solution of the tartarimide or malimide demonstrates an equilibrium surface tension of less than 52 dynes/cm at a concentration of 5 wt % or less in water at 25° C. using the Wilhelmy plate method.

In one aspect of the invention the tartarimides and malimides of the above formulas display excellent ability to reduce equilibrium surface tension while producing little to no foam.

These materials may be prepared by the reaction of primary amines with tartaric acid and malic acid, or tartaric acid and malic acid esters. The reactions are illustrated below:

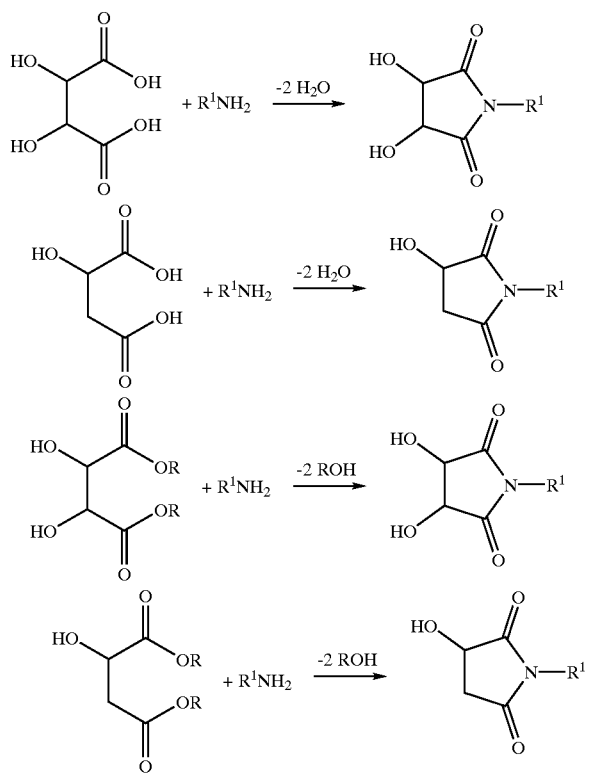

The preparation of the imides may be performed using well-known reactions as taught by A. Ladenburg, *Ber. Dtsch. Chem. Ges.* 1896, 29, 2711 or F. Barrow, et. al., *J. Chem. Soc. (London)*, 1939, 638. The preferred method involves the reaction of tartaric or malic acid with one equivalent of a primary amine and heating to remove the water.

All primary amines or mixtures of primary amines containing the requisite C5 to C10 alkyl substituents may be utilized for the preparation of the N-alkyltartarimides and N-alkylmalimides of this invention, with amines containing 7–10 carbons being preferred and those containing 8–10 carbons being especially preferred. Alkyl groups which are suitable should have sufficient carbon to confer surface activity (i.e. an ability to reduce the surface tension of water) to the material but not enough carbon to decrease the solubility to the extent that the ability of the material to reduce surface tension is insufficient for a particular application. Generally, in the practice of this invention, it is desirable to choose alkyl groups such that the resulting N-alkyltartarimides or N-alkyl-malimides have a solubility that affords the desired surface tension reduction.

The alkyl groups in the tartarimides and malimides of this invention may be linear or branched. Examples of suitable ailkyl groups are n-pentyl, 2-methylbutyl, iso-pentyl, n-hexyl, 2-methylpentyl, 3-methylpentyl, 2-ethylbutyl, 4-methyl-2-pentyl, 2-ethylhexyl, 2-methylhexyl, 5-methylhexyl, 6-methylheptyl, n-heptyl, n-octyl, nonyl, decyl, and so on. Mixtures of the suitable amines may also be used. Those imides which contain a total of 7–10 alkyl carbons are preferred and those containing 8–10 alkyl carbons are most preferred, especially in the cases where $R^1$=2-ethylhexyl and n-decyl.

An amount of N-alkyltartarimide or N-alkylmalimide that is effective for reducing the equilibrium surface tension of the water-based, organic compound-containing composition may range from 0.001 to 20 wt %, preferably 0.01 to 10 wt %, of the aqueous composition. Naturally, the most effective amount will depend on the particular application and the solubility of the tartarimide or malimide.

The alkyltartarimides and alkylmalimides are suitable for use in an aqueous composition comprising in water an inorganic compound which is a mineral ore or a pigment or an organic compound which is a pigment, a polymerizable monomer, such as addition, condensation and vinyl monomers, an oligomeric resin, a polymeric resin, a detergent, a caustic cleaning agent, a herbicide, a fungicide, an insecticide, or a plant growth modifying agent.

In the following water-based organic coating, ink, adhesive, fountain solution, agricultural and photoresist developer compositions containing a tartarimide or malimide according to the invention, the other listed components of such compositions are those materials well known to the workers in the relevant art.

A typical water-based protective or decorative organic coating composition to which the tartarimide and malimide surfactants of the invention may be added would comprise in an aqueous medium 30 to 80 wt % of a coating composition containing the following components:

| Water-Based Organic Coating Composition |
| --- |
| 0 to 50 wt % Pigment Dispersant/Grind Resin |
| 0 to 80 wt % Coloring Pigments/Extender Pigments/Anti-Corrosive Pigments/Other Pigment Types |
| 5 to 99.9 wt % Water-Borne/Water-Dispersible/Water-Soluble Resins |
| 0 to 30 wt % Slip Additives/Antimicrobials/Processing Aids/Defoamers |
| 0 to 50 wt % Coalescing or Other Solvent |
| 0.01 to 10 wt % Surfactant/Wetting Agent/Flow and Leveling Agents |
| 0.01 to 5 wt % N-alkyltartarimide and/or N-alkylmalimide |

A typical water-based ink composition to which the tartarimide and malimide surfactants of the invention may be added would comprise in an aqueous medium 20 to 60 wt % of an ink composition containing the following components:

| Water-Based Ink Composition | |
| --- | --- |
| 1 to 50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-Borne/Water-Dispersible/Water-Soluble Resins |
| 0 to 30 wt % | Coalescing or Other Solvent |
| 0.01 to 10 wt % | Surfactant/Wetting Agent |
| 0.01 to 10 wt % | Processing Aids/Defoamers/Solubilizing Agents |
| 0.01 to 5 wt % | N-alkyltartarimide and/or N-alkylmalimide |

A typical water-based agricultural composition to which the tartarimide and malimide surfactants of the invention may be added would comprise in an aqueous medium 0.01 to 80 wt % of an agricultural composition containing the following components:

| Water-Based Agricultural Composition | |
| --- | --- |
| 0.1 to 50 wt % | Pesticide, Insecticide, Herbicide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.01 to 50 wt % | N-alkyltartarimide and/or N-alkylmalimide |

A typical water-based fountain solution composition for planographic printing would comprise the following components:

| Water-Based Fountain Solution | |
| --- | --- |
| 0.05 to 10 wt % | Film formable, water soluble macromolecule |
| 1 to 25 wt % | Alcohol, glycol, or polyol with 2–12 carbon atoms, water soluble or can be made to be water soluble |
| 0.01 to 20 wt % | Water soluble organic acid, inorganic acid, or a salt thereof |
| 30 to 70 wt % | Water |
| 0.01 to 5 wt % | N-alkyltartarimide and/or N-alkylmalimide |

A typical water-based adhesive composition to which the tartarimide and malimide surfactants of the invention may be added would comprise in an aqueous medium 30 to 65 wt % of an adhesive composition containing the following components:

| Water-Based Adhesive | |
| --- | --- |
| 50 to 99 wt % | Polymeric Resin (SBR, VAE, Acrylic) |
| 0 to 50 wt % | Tackifier |
| 0 to 0.5 wt % | Defoamer |
| 0.5 to 2 wt % | N-alkyltartarimide and/or N-alkylmalimide |

A typical water-based photoresist developer or electronic cleaning composition to which the tartarimide and malimide surfactants of the invention may be added would comprise the following components:

| Water-based Photoresist Developer | |
| --- | --- |
| 0.1 to 3 wt % | Tetramethylammonium Hydroxide |
| 0 to 4 wt % | Phenolic Resin |
| 88 to 99 wt % | Water |
| 10 to 5000 ppm | N-alkyltartarimide and/or N-alkylmalimide |

Examples 1–4 illustrate the synthesis of various N-alkyltartarimides and N-alkylmalimides according to the invention. All N-alkyltartarimides and N-alkylmalimides were synthesized and then characterized by gas chromatography/mass spectrometry, Nuclear Magnetic Resonance (NMR) spectroscopy, and Fourier Transfer-Infrared (FTIR) spectroscopy. All tartarimides and malimides prepared ranged from ~80% to >99% pure.

EXAMPLE 1

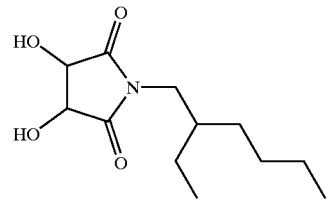

N-2-Ethylhexyl tartarimide was prepared by the reaction of 2-ethylhexyl amine with DL-tartaric acid. The procedure described in U.S. Pat. No. 4,237,022 was followed on a smaller scale. DL-Tartaric acid (10.034 g, 66.853 mmole) and toluene (17.328 g, 188.06 mmole) were weighed into a 250 mL 3-necked round-bottomed flask equipped with a teflon-coated magnetic stir bar. A Dean-Stark trap was placed in the center neck, and a condenser was placed in the neck of the Dean-Stark trap. A nitrogen inlet adapter was placed on the condenser. In the left neck was placed a pressure-equalizing addition funnel containing 2-ethylhexyl amine (8.639 g, 66.84 mmole) and toluene (6.092 g, 66.12 mmole) added to ensure complete transfer of the amine). In the right neck was placed a rubber septum which held a thermocouple. The apparatus was purged with nitrogen for 10–15 minutes and then heated to ~100° C.

Once the tartaric acid slurry had reached 102° C., the amine was added very slowly at a rate of ~0.28 g/min. However, 30 minutes into the addition toluene (13.360 g, 145.00 mmole) was added to the reaction mixture in order to improve mixing of the gelling reaction mixture. Once addition was complete (after 52 min), the cream-colored gelatinous reaction mixture was heated to 120° C. and 29.259 g of water/toluene were collected in the Dean-Stark trap over 4.5 hours. When no further distillate would come over at 120° C., the temperature was increased to 130° C. Similarly, the temperature was increased from 120–1700° C. in 10° C. increments and held at each temperature until no further distillate would come over at that temperature. The temperature was only held at 170° C. for 35 min to avoid dehydrating the tartarimide. In total, 34.90 g of distillate had been collected. On cooling, the orange-brown liquid in the flask solidified to a taffy-like solid (16.264 g). By GC/MS, the major product was identified as the desired tartarimide; however, residual toluene, free amine, and N,N'-dialkyltartramide were also observed in small amount. By $^1$H NMR, water appeared to also be present.

Crude N-2-ethylhexyl tartarimide (7.3686 g) was dissolved in diethyl ether (50 mL) and purified by column chromatography using a 6 cm×24 cm silica gel, 230–400 mesh, 60 A, column. Initially, a 50:50 diethyl ether/hexane solution was used as the eluent and the orange-colored bands due to side products were eluted from the column. After 1.75 h, the eluent was changed to a 75:25 diethyl ether/hexane solution, and the aliquots that contained the desired product were collected during this portion of the chromatography. Finally, after 3 hr, 100% methanol was used as the eluent to remove, all of the remaining residue from the column. The fractions containing the desired product were stripped of solvent on a rotary evaporator and three crops of product that differed slightly in color were obtained. By FTIR, all three crops looked identical with a reasonably sharp OH stretch at 3400 cm$^{-1}$ and a sharp carbonyl stretch at 1685 cm$^{-1}$; none of the crops contained the N,N'-dialkyltartramide or tartaric acid.

|  | Wt of Product | Appearance | Comment |
|---|---|---|---|
| Crop #1 | 2.7738 g | orange-tan color |  |
| Crop #2 | 0.9462 g | yellow-white color | Crop Used for Surface Tension Measurements |
| Crop #3 | 0.4021 g | orange-tan color |  |

EXAMPLE 2

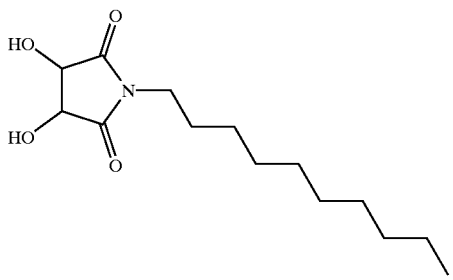

N-Decyl DL-tartarimide was prepared by the reaction of n-decyl amine with DL-tartaric acid. DL-Tartaric acid (10.143 g, 67.579 mmole) and toluene (17.332 g) were weighed into a 250 mL 3-necked round-bottomed flask equipped with a teflon-coated magnetic stir bar. A Claisen adapter was placed in the center neck, a Dean-Stark trap was placed on top of the Claisen adapter, and a condenser was placed in the neck of the Dean-Stark trap. A nitrogen inlet adapter was placed on the condenser. In the left neck was placed a pressure-equalizing addition funnel containing n-decyl amine (10.630 g, 67.578 mmole) and toluene (6.257 g, added to ensure complete transfer of the amine). In the right neck was placed a rubber septum which held a thermocouple. The apparatus was purged with nitrogen for 10–15 minutes and then heated to ~100° C.

Once the tartaric acid slurry had reached 106° C., the amine was added dropwise over 60 minutes. However, the reaction mixture gelled 45 minutes into the addition and additional toluene (13.024 g) was added to the reaction mixture in order to improve mixing. Once addition was complete, more toluene (8.316 g) was added quickly through the addition funnel to ensure complete transfer. The addition funnel was replaced with a glass stopper and the white gelatinous mixture was heated to 115–120° C. A total of 34.491 g of toluene water mixture was collected in the Dean-Stark trap, and heating was continued at a setpoint of 120° C. for 3 hours and at 140° C. for one hour. No additional solvent was collected. After this time, the reaction mixture was cooled to room temperature. On cooling, the orange-brown liquid in the flask solidified to a waxy solid. By GC, the major product was identified as the desired tartarimide. The waxy product was triturated with diethyl ether, filtered, and dried under vacuum to yield 11.132 g (61% yield) of cream-colored solid. By GC, no toluene or amine remained in the product.

EXAMPLE 3

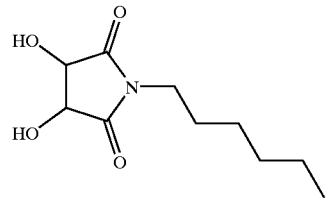

N-hexyl DL-tartarimide was prepared by the reaction of n-hexyl amine with DL-tartaric acid. DL-Tartaric acid (10.026 g, 66.80 mmole) and toluene (17.327 g) were weighed into a 250 mL 3-necked round-bottomed flask equipped with a teflon-coated magnetic stir bar. A Claisen adapter was placed in the center neck, a Dean-Stark trap was placed on top of the Claisen adapter, and a condenser was placed in the neck of the Dean-Stark trap. A nitrogen inlet adapter was placed on the condenser. In the left neck was placed a pressure-equalizing addition funnel containing n-hexyl amine (6.760 g, 66.80 mmole) and toluene (7.936 g, added to ensure complete transfer of the amine). In the right neck was placed a rubber septum which held a thermocouple. The apparatus was purged with nitrogen for 10–15 minutes and then heated to ~100° C.

Once the tartaric acid slurry had reached 100° C., the amine was added dropwise over ~7 minutes. However, the reaction mixture gelled (temperature ~109° C.) and additional toluene (25.977 g) was added to the reaction mixture in order to improve mixing. This broke up the gel to an easily stirred slurry which was heated back up to 105° C. After 18 minutes total reaction time, the reaction again gelled and more toluene (17.360 g) was added to break up the gel. Heating was resumed and the reaction was held at ~100° C. for a total of one hour. After this time, the white slurry was heated to 120° C. and 60.791 g of water/toluene were collected in the Dean-Stark trap over 1 hour and 40 minutes. Suddenly, after 1 hour and 40 minutes at 120° C. the reaction temperature increased from 114–115° C. to ~140° C. The reaction mixture turned yellow and clear at this point. The heating mantle was quickly removed during this exotherm (~5 minutes) and then re-applied as the temperature fell below 125° C. Heating was continued at a setpoint of 120° C. for approximately 4 hours. After this time, the reaction mixture was cooled to room temperature. On cooling, the orange-brown liquid in the flask solidified to a waxy solid. By GC, the major product was identified as the desired tartarimide; however, residual toluene, free amine, and the ditartramide were also observed in small amount. The waxy product was triturated with diethyl ether (5×50 mL) to yield 13.72 g (63.74 mmole, 95% yield) of cream-colored solid. By GC, no toluene or amine remained in the product, but a small amount of the N,N'-dialkyltartramide was present. By NMR, the product appears to be 90% N-hexyl DL-tartarimide and 10% N,N'-di-n-hexyl DL-tartramide.

EXAMPLE 4

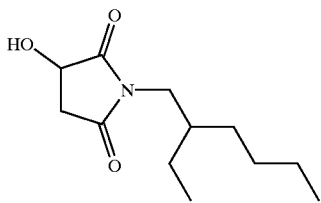

N-2-Ethylhexyl DL-malimide was prepared by the reaction of 2-ethylhexyl amine with DL-malic acid. DL-Malic acid (10.327 g, 77.015 mmole) and toluene (40 mL) were weighed into a 250 mL 3-necked round-bottomed flask equipped with a teflon-coated magnetic stir bar. A Claisen adapter was placed in the center neck, a Dean-Stark trap was placed on top of the Claisen adapter, and a condenser was placed in the neck of the Dean-Stark trap. A nitrogen inlet adapter was placed on the condenser. In the left neck was placed a pressure-equalizing addition funnel containing 2-ethylhexyl amine (9.955 g, 77.02 mmole) and toluene (10 mL, added to ensure complete transfer of the amine). In the right neck was placed a rubber septum which held a thermocouple. The apparatus was purged with nitrogen for 10–15 minutes and then heated to ~100° C.

Once the malic acid slurry had reached 100° C., the amine was added dropwise over 34 minutes. Additional toluene (10 mL) was added via the addition funnel after all of the amine had been added to ensure complete transfer. Most, but not all, of the malic acid appeared to have dissolved by the time addition was complete. The reaction mixture was heated at 100° C. for a total of one hour and then the set point was increased to 120° C., and then to 125° C., in an attempt to remove the toluene/water azeotrope. However, it took ~4.5 hr of heating at a temperature >120° C. before any solvent began to come over in the Dean-Stark trap. A total of 38.497 g of toluene/water was collected over 7 hours of heating. By FTIR, the major product appeared to be the half amide/half acid.

The reaction mixture was cooled to ambient temperature overnight and then re-heated to 140° C. A total of 3.261 g more toluene/water were removed after 7 hours of heating at 140° C. By FTIR, the imide appeared to be the major product.

The viscous orange liquid product was dissolved in diethyl ether (50 mL) and the ether solution was shaken with saturated sodium bicarbonate solution (50 mL). The ether layer was separated, dried over magnesium sulfate, filtered and evaporated to yield an orange wax. By GC/MS, the major product (~89%) was the desired N-2-ethyl-hexyl malimide, and the largest side product (~10%) was the N-2-ethylhexyl maleimide that is formed via dehydration of the desired malimide. Small amounts of N,N'-di-2-ethylhexyl malamide and the addition product of 2-ethylhexyl amine across the double bond of N-2-ethylhexyl maleimide were also detected.

EXAMPLES 5–8

Saturated solutions containing <0.1 wt % of the materials of Examples 1–4 in distilled water were prepared. After shaking the solutions for ~24 hours, the undissolved material was removed via filtration. Equilibrium surface tension data were obtained using the Wilhelmy plate method.

The limiting equilibrium surface tension data are provided in Table 1. The limiting surface tensions represent the lowest surface tensions in water which can be achieved for a given surfactant regardless of the amount of surfactant used and is used to evaluate the effectiveness of a surfactant. Lower surface tensions would allow the elimination of defects upon application of a formulation onto low energy surfaces.

TABLE 1

| Example | Compound | Limiting EST (dyne/cm) |
|---|---|---|
|  | Water | 72.1 |
| 5 | N-2-Ethylhexyl DL-Tartarimide (Ex 1) | 34.2 |
| 6 | N-Decyl DL-Tartarimide (Ex 2) | 32.0 |
| 7 | N-Hexyl DL-Tartarimide (Ex 3) | 51.8 |
| 8 | N-2-Ethylhexyl DL-Malimide (Ex 4) | 37.2 |

The data in Table 1 illustrate that certain N-alkyltartarimides and N-alkyl-malimides have the ability to reduce the surface tension of aqueous compositions. Examples 5–8 demonstrate that N-alkyltartarimides and N-alkylmalimides in which the alkyl groups contain 6–10 carbon atoms each exhibited surface tension values of less than 52 dyne/cm at a concentration of ≦0.1 wt % in water at 25° C. N-2-Ethylhexyl tartarimide (Ex 1), N-decyl tartarimide (Ex 2), and N-2-ethylhexyl malimide (Ex 4) were particularly effective at lowering the equilibrium surface tension of water. Therefore, the N-alkyltartarimides and N-alkylmalimides which contain alkyl groups with 8–10 carbon atoms are most preferred for the reduction of surface tension of water in water-based, organic compound containing compositions, including waterborne coatings, inks, adhesives, fountain solutions and agricultural formulations. However, ultimately the choice of N-alkyltartarimide or N-alkylmalimide will depend upon the application.

EXAMPLES 9–13

The foaming properties of aqueous solutions of N-2-ethylhexyl tartarimide (Ex 1), N-decyl tartarimide (Ex 2), N-2-ethylhexyl malimide (Ex 4) and two representative nonionic surfactants, a commercial nonylphenol 15 mole ethoxylate surfactant and a commercial C8 alkyl glucoside surfactant, were examined using a procedure based upon ASTM D 1173-53. The results are reported in Table 2.

In this test, a 0.1 wt % aqueous mixtures of the tartramides and malimide were prepared, any undissolved solids were filtered off, and the filtrate was added from an elevated glass pipette to a glass receiver containing the same filtrate. Regarding the commercial materials, a 0.1 wt % solution of the surfactant was added from an elevated glass pipette to a glass receiver containing the same solution. The foam height was measured at the completion of the addition ("Initial Foam Height") and the time required for the foam to dissipate at the air-liquid interface ("Time to 0 Foam") was recorded. This test provides a comparison between the foaming characteristics of various surfactants. In general, in coatings, inks, adhesives and agricultural formulations, foam is undesirable because it complicates handling and can lead to coating and print defects, and to inefficient application of agricultural materials.

TABLE 2

| Ex | Surfactant | Initial Foam (cm) | Foam after 5 min (cm) | Time to zero foam |
|----|------------|-------------------|------------------------|-------------------|
| 9  | N-2-Ethylhexyl DL-Tartarimide (Ex 1) | 0 cm | 0 cm | 0 sec |
| 10 | N-Decyl DL-Tartarimide (Ex 2) | 3.2 cm | 0 cm | 3.8 min |
| 11 | N-2-Ethylhexyl DL-Malimide (Ex 4) | 0 cm | 0 cm | 0 sec |
| 12 | Nonylphenol 15 mole ethoxylate | 5 cm | 4 cm | >5 min |
| 13 | C8 Alkyl glucoside | 1.9 cm | 1.0 cm | 37 min |

The data in Table 2 show that the compounds of this invention formed very little initial foam and that the foam which formed dissipated very quickly. In addition to their ability to reduce the surface tension of organic-containing aqueous, N-alkyltartarimides and N-alkylmalimides surfactants have desirable foam properties with respect to their use in coatings, inks, adhesives, agricultural and electronic cleaning formulations.

The ability to control foam is advantageous in many applications, including coatings, inks, adhesives, fountain solutions, agricultural and electronic cleaning formulations. A drawback to the use of many conventional surfactants in coatings, inks, adhesives, fountain solutions, agricultural formulations and electronic chemicals is the formation of considerable quantities of long-lasting foam in these systems. For such applications, it is desired that a surfactant form as little foam as possible and that the foam which forms dissipates quickly.

STATEMENT OF INDUSTRIAL APPLICATION

The invention provides compositions suitable for reducing the equilibrium surface tension in water-based coating, ink, adhesive, fountain solution, agricultural, electronic cleaning and photoresist developer compositions.

We claim:

1. In a method for applying a coating of a water-based composition to a surface to partially or fully coat the surface, the water-based composition being selected from the group consisting of aqueous organic coating, ink, adhesive, fountain solution, agricultural and electronics cleaning compositions and containing an effective amount of a surfactant for reducing the equilibrium surface tension of the composition, the improvement which comprises employing as the surfactant an N-alylimide of tartaric acid and/or an N-alkylimide of malic acid of the following structures, respectively:

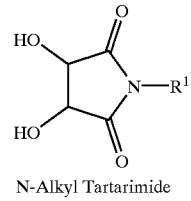
N-Alkyl Tartarimide

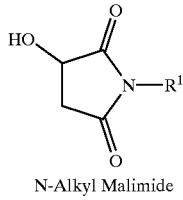
N-Alkyl Malimide where $R^1$ is a C5 to C10 alkyl group, the surfactant reducing surface tension and controlling foam.

2. The method of claim 1 in which the N-alkyltartarimide and/or N-alkyimalimide is present at 0.001 to 20 wt % of the water-based composition.

3. The method of claim 2 in which an aqueous solution of each of the N-alkyltartarimide and/or N-alkylmalimide demonstrates a equilibrium surface tension of less than 52 dynes/cm at a concentration of no more than 5 wt % in water at 25° C. according to the Wilhelmy plate method.

4. The method of claim 1 in which $R^1$ is a C7 to C10 alkyl group.

5. The method of claim 4 in which the surfactant is an N-alkyltartarimide.

6. The method of claim 5 in which $R^1$ is 2-ethylhexyl.

7. The method of claim 5 in which $R^1$ is n-decyl.

8. The method of claim 4 in which the surfactant is an N-alkylmalimide.

9. The method of claim 8 in which $R^1$ is 2-ethylhexyl.

10. The method of claim 4 in which $R^1$ is a C8 to C10 alkyl group.

* * * * *